United States Patent
Venter et al.

(10) Patent No.: US 9,556,413 B2
(45) Date of Patent: Jan. 31, 2017

(54) SYSTEM AND METHODS FOR ANAEROBIC ENVIRONMENTAL MICROBIAL COMPARTMENTALIZED CULTIVATION

(75) Inventors: J. Craig Venter, La Jolla, CA (US); Eric J. Mathur, San Diego, CA (US); Gerardo Vicente Toledo, Belmont, MA (US); Hwai Wen Chang, San Marcos, CA (US); Wayne A. Green, Encinitas, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 1882 days.

(21) Appl. No.: 12/532,403

(22) PCT Filed: Mar. 21, 2008

(86) PCT No.: PCT/US2008/057919
§ 371 (c)(1),
(2), (4) Date: Mar. 15, 2010

(87) PCT Pub. No.: WO2008/116187
PCT Pub. Date: Sep. 25, 2008

(65) Prior Publication Data
US 2010/0330651 A1    Dec. 30, 2010

Related U.S. Application Data

(60) Provisional application No. 60/919,632, filed on Mar. 22, 2007.

(51) Int. Cl.
*C12M 1/34* (2006.01)
*C12N 1/20* (2006.01)
(Continued)

(52) U.S. Cl.
CPC ............... *C12N 1/20* (2013.01); *C12M 23/44* (2013.01); *C12M 45/03* (2013.01); *C12M 47/04* (2013.01)

(58) Field of Classification Search
CPC .......... C12N 1/20; C12M 23/44; C12M 45/03; C12M 47/04
(Continued)

(56) References Cited

U.S. PATENT DOCUMENTS 4,111,753 A * 9/1978 Folsom et al. .................... 435/3
4,279,345 A * 7/1981 Allred ............................ 209/3.2
(Continued)

FOREIGN PATENT DOCUMENTS

| GB | 2 174 714 A | 11/1986 |
|----|-------------|---------|
| JP | 05084096 A * | 4/1993 |
| WO | WO 2008/116187 A1 | 9/2008 |

OTHER PUBLICATIONS

Katsuragi et al., "Gel microdroplet technique leaving microorganisms alive for sorting by flow cytometry", Journal of Microbiological Methods 42:81-86, 2000.
(Continued)

*Primary Examiner* — Michael Hobbs
(74) *Attorney, Agent, or Firm* — DLA Piper LLP (US)

(57) ABSTRACT

The invention described below relates to an enclosed cell sorting device and methods of using the device. The device is constructed so that the entire process of cell sorting can be conducted under fully anaerobic conditions to retain viability of anaerobic cells before, during, and after cell sorting. This is accomplished by creating an anaerobic atmosphere for the high speed cell sorter and all its components and by the use of airlocks that allow the introduction of anaerobic containers into the chamber containing the sample.

10 Claims, 4 Drawing Sheets

(51) Int. Cl.
 *C12M 3/00* (2006.01)
 *C12M 1/00* (2006.01)
(58) Field of Classification Search
 USPC .............................................. 435/243, 283.1
 See application file for complete search history.

(56) References Cited

U.S. PATENT DOCUMENTS

| | | | |
|---|---|---|---|
| 5,641,457 A * | 6/1997 | Vardanega et al. ......... | 422/82.01 |
| 5,776,781 A | 7/1998 | Vardanega et al. | |
| 6,780,377 B2 | 8/2004 | Hall et al. | |
| 6,881,580 B2 | 4/2005 | Hall et al. | |
| 7,303,678 B2 | 12/2007 | Bradford et al. | |
| 2005/0019949 A1 * | 1/2005 | Hall et al. ..................... | 436/174 |
| 2005/0070005 A1 | 3/2005 | Keller | |
| 2005/0112541 A1 * | 5/2005 | Durack et al. .................... | 435/2 |
| 2006/0004236 A1 | 1/2006 | Barvincak | |
| 2006/0099707 A1 | 5/2006 | Nelson et al. | |
| 2006/0219632 A1 | 10/2006 | Bradford et al. | |
| 2006/0223160 A1 | 10/2006 | Vanzin | |

OTHER PUBLICATIONS

Manome et al., "Application of gel microdroplet and flow cytometry techniques to selective enrichment of non-growing bacterial cells", FEMS Microbiology Letters 197:29-33, 2001.
Nir et al., "Single-Cell Entrapment and Microcolony Development within Uniform Microspheres Amenable to Flow Cytometry", Applied and Environmental Microbiology, 56(9):2870-2875. 1990.
Zengler et al., "Cultivating the uncultured", PNAS 99(24):15681-15686, 2002.
European Search Report from EP 08 74 4213, Dec. 27, 2011. 7 pages.
Japanese Office Action with English translation, issued on Nov. 2, 2015, regarding JP 2009-554782.
JP 2009-554782 English translation of Office Action, Jul. 7, 2014.

* cited by examiner

FIG. 4A
FIG. 4B
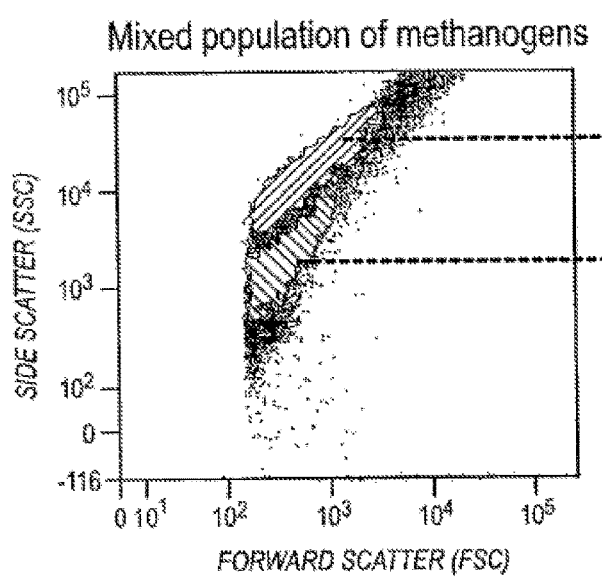
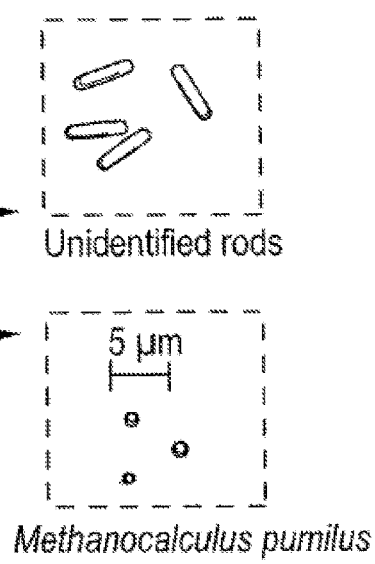
FIGS. 4A-B

SYSTEM AND METHODS FOR ANAEROBIC ENVIRONMENTAL MICROBIAL COMPARTMENTALIZED CULTIVATION

CROSS-REFERENCE TO RELATED APPLICATIONS

This application is the national phase of PCT application PCT/US2008/057919 having an international filing date of Mar. 21, 2008, which claims benefit of U.S. provisional patent application No. 60/919,632, filed Mar. 22, 2007. The contents of the above patent applications are incorporated by reference herein in their entirety.

TECHNICAL FIELD

Exemplary systems and methods relate generally to environmental microbiology, and more particularly to systems and methods for anaerobic environmental microbial, compartmentalization cultivation (referred to herein as "EMCC").

BACKGROUND ART

The microbial diversity of the planet is primarily represented by uncultivated species that are not amenable to growth under laboratory conditions. Obligate anaerobes are a particular example of microbes that are not amenable to cultivation using standard laboratory techniques as these cells are either completely or nearly completely intolerant to oxygen exposure. Obligate anaerobic microorganisms employ anaerobic respiration that may include fermentative routes to obtain energy. Some of these pathways include propionic acid fermentation, butyric acid fermentation, mixed acid fermentation, butanediol fermentation, Stickland fermentation, acetogenesis or methanogenesis. There is a great deal of metabolic diversity exhibited by anaerobic microorganisms, some of which may lead to fermentation products such as wine. More recently, there is an increased interest in the production of alcohols such as ethanol and butanol derived from plant materials to produce biofuels to substitute petrochemical-derived combustibles as vehicle propellant.

Some of these previously uncultivated anaerobes are thought to mediate processes in the environment linked to global carbon and energy fluxes, including the production methane, biodiesel, hydrogen and alcohols from carbon sources. Methane extracted from coal deposits, known as coal bed methane, from which commercial methane gas is produced, is thought to be the product (in whole or in part) of such anaerobic organisms. New methods for isolating and cultivating novel anaerobic microorganisms are desirable, since such organisms have a variety of useful applications. For example, the ability to cultivate novel anaerobic species participating in the methane production at coal bed sites will allow for increased methane production.

The isolation and cultivation of anaerobic microorganisms has been limited to date by the lack of available equipment and culture vessels providing anoxic atmospheres on which oxygen sensitive cells divide and cultures may be established. High speed cell sorters, such as flow cytometers, have been used for the selection and downstream cultivation of aerobic microorganisms, and in some cases instrument modifications have been made to allow cell sorting under controlled atmospheres, including anaerobic gas mixtures. However the complete operation of a cell sorting device in a contained environment has never been demonstrated. This is thought to be primarily due to their relatively large dimensions and complex ancillary infrastructure required for the operation of typical cell sorting devices, such as water cooling systems, pressurized air, and very sensitive 3D laser alignment.

Conventional gel microdroplet (or "GMD") encapsulation and flow cytometry have been used for studying aerobic bacteria (Nir et al. 1990 Appl. Environ. Microbiol. 56:2870-2875; Katsuragi et al., 2000 J. Microbiol. Meth. 42:81-86; Manome et al. 2001 FEMS Microbiol. Lett. 197: 29-33). Zengler et. al. (2002 PNAS, 99:15681-15686) used GMDs for growth of novel aerobic bacteria from the environment demonstrating the ability of the GMD technique combined with flow cytometry to cultivate previously uncultured microorganisms. The authors also grew one strain of the strict anaerobe *Methanococcus thermolithotrophicus* from the American Type Culture Collection in GMDs, but did not demonstrate the ability to sort this anaerobically.

One limitation to sorting cells anaerobically is the inability to perform cell sorting under anoxic conditions. Dissolved oxygen present in the fluidics and during sample injection exposes cells to oxygen levels not permissible for anaerobic growth. Establishment of anaerobic cultures using aerobic procedures, such as those found in existing high speed cell sorting, is hindered by the cellular damage produced by oxygen upon brief exposure time. Thus, the vast majority of strict anaerobic cells cannot be sorted using existing technology. As a consequence, work to date conducting aerobic or partially anaerobic cell sorting of anaerobic cells has resulted in an incomplete cultivation of the indigenous populations.

An example of a partially enclosed device and method for processing cells is described in U.S. Pat. No. 6,780,377 (hereinafter "the '377 patent"). The '377 patent provides an environmental containment system fitted to a DAKO cell sorter to sort cells under a specific atmosphere including those suitable for the cultivation of strict anaerobic microorganisms. A major limitation of this environmental containment system is that the sample cells are exposed to oxygen at multiple points during processing. First, to sort obligate anaerobes, the sample needs to be prepared and handled under anaerobic conditions. This implies at a minimum that the transportation of the sample between an anaerobic chamber used to prepare the sample and the cell sorting system needs to be performed in an oxygen-free environment. This point is not discussed in the '377 patent. Second, introduction of the sample into the cell sorting device must also take place in an oxygen-free environment. As such, the sample port of the cell sorter needs to be free of oxygen. The '377 patent does not considered the sample injection port as part of the anaerobic environment. As a result, a sample processed using the invention described in that patent is exposed to oxygen from the air prior to cytometry and sorting. Third, the fluidics driving the laminar flow and producing the envelope and droplets used during cell sorting need to be oxygen free. The necessity of maintain not only an anaerobic gas but the use of anaerobic fluids, that is, through sparging anaerobic gas into a suitable gas impermeable container as part of the process is not addressed and it is only mentioned the potential for "adjustably controlling the environment surrounding the process (es) of fluid stream generation," droplet formation, droplet separation and droplet collection." In practical terms, the use of fluids with low amounts of oxygen (few parts per million) can be toxic for anaerobic microorganisms and the fluids used to drive the sample and droplet formation need to absolutely oxygen free. In view of these systemic limitations, it is clear that the '377 patent does not teach a completely anoxic system.

What is needed is a cell sorting system, the components of which are completely self-contained, which protects organisms from exposure to oxygen prior to, during, and after the cell sorting process.

SUMMARY OF THE INVENTION

The method of the present invention allows the high throughput isolation and cultivation of useful anaerobic microorganisms. The method is performed under anoxic conditions, allowing isolation and growth of strict anaerobic cells. In one embodiment, high speed cell sorters are encased in an anaerobic chamber, allowing strict anaerobic cells to be sorted and subsequently to grow under the described conditions. The use of anaerobic environmental microbial compartmentalize cultivation (EMCC) of the described invention on environmental samples resulted in the cultivation of strict anaerobes such as the methanogen *Methanocalculus pumilus* that may mediate valuable commercial processes, such as methane production in coal seams.

Exemplary systems and methods allow the high throughput isolation and cultivation of useful anaerobic microorganisms. A method is performed under anoxic conditions, allowing isolation and growth of strict anaerobic cells. In one embodiment, high speed cell sorters are encased in an anaerobic chamber, allowing strict anaerobic cells to be sorted and subsequently to grow under the described conditions. The use of anaerobic EMCC on environmental samples results in cultures of previously uncultivated anaerobic lineages that may mediate valuable commercial processes, such as methane production in coal bed seams.

Additional uses for the present technology provide to the handling of biohazardous samples in a completely contained environment without the expense of constructing entire rooms with contained airflow systems.

The process, according to various exemplary methods, is performed under fully anaerobic conditions to retain viability of anaerobic cells after cell sorting. This is accomplished by creating an anaerobic atmosphere for the high speed cell sorter, such as a flow cytometer. The modifications for anaerobic cell sorting evolved only recently due to novel cell sorting technology that allowed a compact design and portability in sorters such as the Becton Dickinson FACSAria that can fit in an anaerobic chamber. Prior to this, high speed cell sorters, such as the model MoFlo by DAKO were not amenable for encasing and operation inside a hood (for example, a great deal of manual dials and knobs need to be accessed for proper instrument set-up and operation). In addition, the relatively large instrument footprint and the need for water-cooled lasers made the encasing in a enclosed cell sorting system unattractive. The systems and methods provided herein solve these problems and provide a new technology that will enhance the ability to cultivate in vitro strict anaerobic cells not previously cultivated.

Various exemplary methods are provided for the cultivation of indigenous anaerobic microorganisms. One method uses compartments that provide support for the establishment of a microbial colony consisting of two or more cells, derived from one or more encapsulated cells. Original samples may be collected from terrestrial, aerial and aquatic biotopes. These samples contain microorganisms, including Archaea, Bacteria and Eukarya, including some species that may be commensals or symbionts of vertebrate and invertebrate animals living in their internal organs such as the digestive tracts or on their external surfaces such as skins and teguments. Plant tissues such as roots, leaves and stems may also be used as samples as they may be the source of the indigenous cells. The disclosed Environmental Microbial Compartmentalized Cultivation (EMCC) process may be applied to these samples and is optimized for the isolation of strict or facultative anaerobic species. Steps in the process are optimally conducted under fully anaerobic conditions allowing the recovery of primarily novel strains and assemblages as compared to the use of traditional cultivation techniques such as agar plates.

BRIEF DESCRIPTION OF THE DRAWINGS

FIG. 4A show a scatter plot of a mixed population of methanogens. FIG. 4B shows an illustration of unidentified rods and cocci, the latter corresponding to the methanogen *Methanocalculus pumilus*.

DETAILED DESCRIPTION OF THE INVENTION

The invention described below relates to an enclosed cell sorting device and methods of using the device. The device is constructed so that the entire process of cell sorting can be conducted under fully anaerobic conditions to retain viability of anaerobic cells before, during, and after cell sorting. This is accomplished by creating an anaerobic atmosphere for the high speed cell sorter and all its components and by the use of airlocks and vestibules that allow the introduction of anaerobic containers into the chamber containing the sample. These airlocks and vestibules are typically used in the isolation of anaerobic microorganisms by agar plates and enrichments.

The Device

Figure 1:
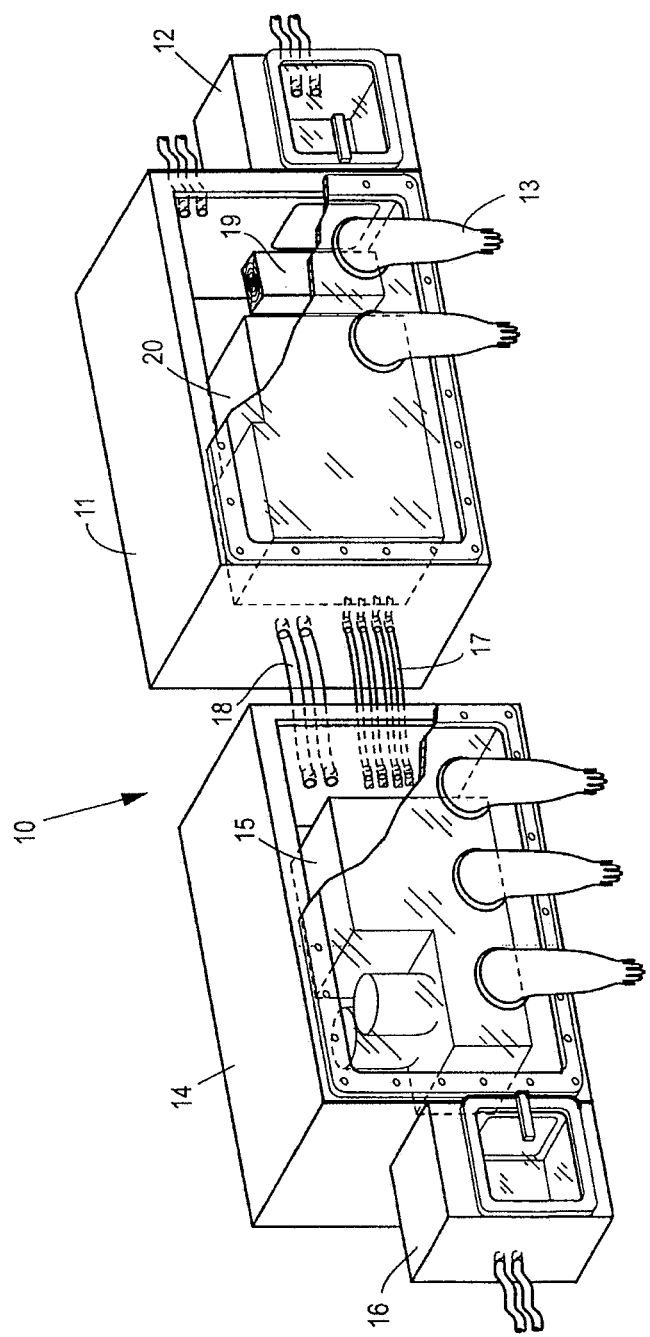
FIG. 1 shows a schematic view of the cell sorting apparatus.
Figure 2:
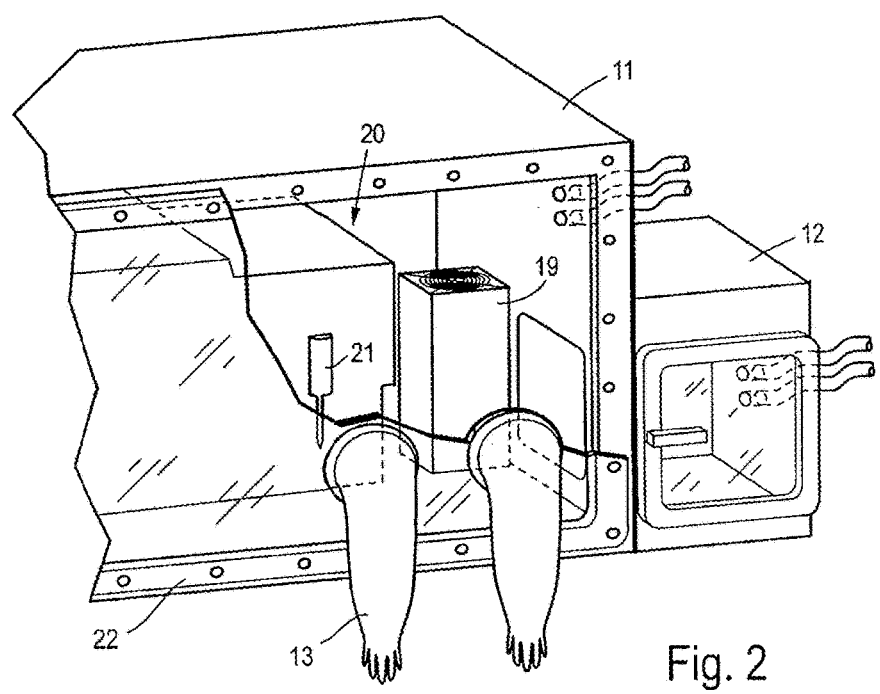
FIG. 2 schematic view of the cell sorting compartment.
Figure 3:
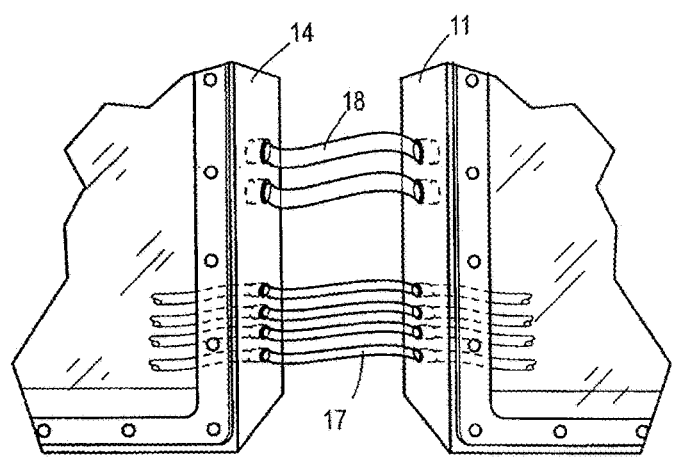
FIG. 3 schematic view of the connection between fluidics compartment and the cell sorting compartment.

An exemplary device is shown in FIGS. 1-3. FIG. 1 shows an anoxic cell sorting chamber (10) comprising a cell sorting compartment (11) and a fluidics compartment (14). The cell sorting compartment comprises one or more chamber gloves (13) which allow the operator to manipulate samples and to make adjustments to the cell sorting equipment without disrupting the atmospheric conditions within cell sorting compartment. The cell sorting compartment further comprises a sample handling vestibule (12) which is connected to the external wall of the cell sorting compartment via an air lock. Sample containers are placed within the sample handling vestibule through an external air lock. The sample handling vestibule is connected to various pumps, gas sources, and sensing equipment which allow for the atmosphere within the vestibule to be regulated and controlled. These features allow for the creation of an anoxic atmosphere within the sample handling vestibule.

The fluidics compartment (14) contains a fluidics pump (15) that can drive the operation of the cell sorter using a compressor. Alternatively, fluids used by the cell sorter can be driven using a suitable gas at the needed pressure and controlled by a regulator. The fluidics compartment preferably contains reservoirs with the various solutions used during the cell sorting procedure such as a suitable anaerobic sheath fluid (PBS buffer, saline solution, artificial sea water), ethanol for decontamination. The compartment can also contain a waste tank which is designed to collect the used sheath and sample and also suitable decontaminating solutions. A fluidics vestibule (16) similar in function to the sample handling vestibule can also form part of the fluidics compartment in order to introduce or extract materials from the compartment without exposing the system to oxygen from air or interrupting the instrument operation. Segregation of the fluidics portion of the device from the cell sorting equipment is preferred for a number of practical reasons. For example, in operation, the fluid pumps can generate excessive amounts of heat which must be dealt with to maintain an environment suitable for cell sorting. This heat, if not dissipated can be transferred to the fluids used during the cell sorting procedure, which may damage the cells being sorted. Vibrations and noise from the pump systems can also be harmful to the functioning of the cell sorting system. As such, appropriate dampening systems may need to be employed in the fluidics compartment. Alternatively, an anaerobic gas source, preferably external to the fluidics compartment, can be used to drive the solutions used during the cell sorting procedure through the system.

In a preferred embodiment the fluidics compartment is linked to the cell sorting compartment in a manner that allows for the atmosphere of the two compartments, including atmospheric pressures therein, to come to equilibrium. This preferred embodiment is illustrated in FIG. 1, which illustrates the two compartments linked via fluidic tubes (17) and one or more chamber equalization tubes (18). Temperature control units (19) can be connected to one or both compartments to regulate temperature in the compartments as needed.

FIG. 2 provides a more detailed view of the cell sorting compartment (11). The sample handling vestibule (12) is clearly shown along with the air locks that permit sample handling. The chamber gloves (13) are also shown. The cell sorter (20) is positioned within the compartment to permit the operator to easily access samples from the sample handling vestibule, manipulate them appropriately, and introduce the samples into the sample injector (21) of the cell sorter. Also illustrated in this figure the removable panel (22) that forms the front portion of the cell sorting compartment. A similar panel is also present as part of the fluidics compartment.

FIG. 3 provides a more detailed view of the connections between the cell sorting compartment (11) and the fluidics compartment (14). The fluidics tubes (17) and the chamber equalization tubes (18) are shown.

The compartments discussed above and used to house the relevant instruments may be made of any material that is strong enough to safely contain the equipment. In a preferred embodiment, such material is aluminum, although any material of sufficient tensile strength is contemplated for use with the described invention. The panels in both the cell sorting and fluidics compartments are removable to allow instrument service and fluidics refilling. It has been demonstrated that contrary to expectations, a typical cell sorter contained in an anoxic environment functions in the same way as if it was not so compartmentalized, validating the usefulness of the described invention. For example, heat generated by the lasers and the mechanical parts do not increase significantly the temperature inside the chamber.

Environmental Microbial Compartmentalized Cultivation (EMCC)

Environmental Microbial Compartmentalized Cultivation (EMCC) is a process that employs compartmentalization of various cell sorting system components to create a desired environment within which microorganisms can be sorted in preparation for subsequent cultivation. In preferred embodiments the environment in which microorganisms are sorted is an anaerobic one. Anaerobic EMCC may be used for the determination of anaerobe function, including growth, lack of growth, drug susceptibility, secretion of molecules or proteins, specific enzyme activity, production of small metabolites, and/or for determination of anaerobe composition including, surface markers, internal proteins, and/or nucleic acid sequences. This method is useful, for example, for the isolation of microorganisms responsible for methane production in coal bed seams. The method provides access to in vitro cultivation and optimization of microbial assemblages composed of cellulolytic, fermentative, acetogen and methanogen species. Members belonging to these microbial groups grow in coal seams and interact synergistically to produce methane that may be exploited for commercial use as natural gas.

The disclosed system can easily be adapted for use with an aerobic environment, however one that is completely segregated from the surrounding room. The contained atmosphere allows for the handling and sorting of biohazardous samples without the expense of constructing large laboratory fixtures that are normally associated with such experiments, for example by using biosafety hoods for infectious agents level 3.

The method of anaerobic EMCC may be carried out in several steps. For example, collection of source samples may be followed by compartmentalization of the cells, incubation of the cells and cell sorting. Identified and cultured organisms may be used in a variety of applications. One or more or all of the steps are performed under an anaerobic atmosphere, such as one composed of hydrogen, carbon dioxide and/or nitrogen.

Sample Collection

In one exemplary embodiment, sample collection is performed under anaerobic conditions by reducing the oxygen present with sodium sulfide and/or cysteine at a final concentration of 0.5 g/L in a bottle or culture vessel fitted with butyl stoppers to prevent air diffusion into the reduced sample. The types of environmental samples include aquatic, soils, sediments, microbial communities associated to digestive tracts of insects and other invertebrates among others. Alternatively to the use of sodium sulfide samples can be gassed with nitrogen to reduce the dissolved oxygen or processed in an anaerobic chamber on the field and deposited into anaerobic jars with chemical catalyst to quench the oxygen present. A variety of oxygen sensing devices are well known to those of ordinary skill in the art and can be used to monitor the presence of absence of an anaerobic environment with a particular space, such as a sample collection chamber.

Sample Compartmentalization

In another embodiment, compartmentalization may be performed using cell encapsulation by the use of materials such as gel microdroplets. Gel microdroplets (GMDs) are approximately 10 to 300 micrometer in diameter, and may use either autofluorescent cell properties such as those observed in cells with the natural presence of pigments or by the addition of a fluorescent dye to analyze rapidly the amount of specific or generic material in each gel microdroplet. Gel microdroplets are generally aqueous microdrops containing a biocompatible matrix such as agarose, agar, sodium alginate, and GELRITE (in the case of temperatures higher than 70° C.) among others and may be used while surrounded either by a non-aqueous medium (closed GMDs) or by an aqueous medium (open GMDs). Microencapsulation methods, such as GMDs, serve to compartmentalize the environment of one or more cells to facilitate production of massively parallel culturing conditions. The anaerobic progeny may be cultivated and retained next to each other within a single GMD allowing manipulation and manual sorting using an anaerobic micromanipulation system, and may be handled much like non-encapsulated cell suspensions (e.g., suspended, pipetted, centrifuged). GMDs may rapidly exchange molecules with the external medium by diffusion, which allows rapid changes in the exposure of individual anaerobic cells and cell assemblages within GMDs to many different conditions, incorporated herein in their entirety.

Other types of compartmentalization include the use of nucleating agents. These may be fluorescent polystyrene beads of 5 pm in diameter coated with growth media that will promote the microbial colonization on its surface and the establishment of microbial cultures as assemblages or single isolates.

Incubation

In one exemplary embodiment, assays may be performed within many gel microdrops simultaneously by culturing cells encapsulated in gel microdroplets in media for a period of time to permit cell division or protein secretion to occur. This period is typically from 30 min to 24 hrs for cell division and 30 min to 3 hours for assay development. The incubation is initiated with single cells compartmentalized into microbeads or GMDs with the purpose of establishing a clonal population derived from a single cell or a microbial assemblage as result of entrapping a plurality of environmental cells per microbead. The incubation is conducted either in closed systems such as wide-mouth glass bottles fitted with butyl stoppers that prevent oxygen to diffuse into the culture vessel, glass tubes with butyl stoppers also known as Hungate type tubes, and/or Balch tubes with rubber septa. Closed incubations are preferred in cases where the temperature needs to be regulated at higher or lower ambient temperatures hence requiring the use of incubators with temperature control. The entrapped cells may be grown in a rotatory shaker at speeds between 0 to 200 RPM. Alternatively it is possible to use open systems where the media flows through the system in order to allow cells to uptake nutrients and remove waste products. These open incubation systems are fitted with filters of a pore size adequate to retain microbeads but that allow cells not entrapped to be flushed aw-a y from the cultivation vessel in order to conduct open incubations anaerobically, all or some equipment may be enclosed in an anaerobic chamber to prevent oxygen exposure.

According to various exemplary systems and methods, other assay methods utilizing compartmentalization technologies may be employed. For example, microdroplets containing anaerobes are treated with a drug or agent that is a candidate drug before and/or during the incubation period and compared with a control population of untreated microdrops containing anaerobes. If comparison between treated and control anaerobes indicates a different level of secretion of a protein of interest, it may be concluded that the drug or candidate drug affects the level of secretion of this protein. Information may be useful in establishing activity of a candidate agent or in determining mechanism of a drug already known to be effective.

In another embodiment, after incubation to allow secretion, one or more detection reagents may be added, one for each secreted protein or anaerobe-surface marker to be detected. The detection reagent binds to a protein to which it has specific affinity that has been captured by the web.

After binding of detection reagent(s) and generation of signal, the signal may be detected by a variety of approaches. In one approach, gel microdroplets are deposited on a glass or plastic surface, such as a microscope slide, or Petri dish. The microdrops adhere to the support and may be arranged in any format to facilitate analysis. The microdroplets may then be individually examined under a microscope for one of more different labels. Detection may be via fluorescence, chemiluminescence, or color of secreted molecules. Digital imaging systems have made it possible to examine anaerobe activity with increasingly higher resolution.

Automated microscope-based systems driven by value added software are now common research tools. These systems share a number of common features, including the ability' to acquire and store fluorescent images, image enhancement, calibration and thresholding (discrimination) options, and system automation and device control. Microscopic images are digitized into a matrix of small regions called picture elements of pixels. The measurement of the brightness at each pixel is stored and then processed to generate an enhanced image. Image analysis systems are distinctive in the type of processing used for image enhancement and the level of resolution available.

Anaerobic Cell Sorting

In one embodiment, cultures or cells, including isolation of microdroplets containing grown encapsulated cells of interest, may be performed using a cell sorter (20) within a controlled environment. According to one exemplary method, cell sorting may be carried out anaerobically by placing the separating device, such as a bench top high speed cell sorter, into an anaerobic chamber flushed with gas, such as nitrogen gas or anaerobic gas mix composed of hydrogen, carbon dioxide and nitrogen, to provide anaerobic conditions. Previously, this process was not conducted under totally anoxic conditions (e.g., providing a sample that is maintained in an anoxic environment prior to sample injection, after injection, and throughout the cell sorting process) because the complete equipment required to sort cells efficiently was not amenable to encasing in an enclosed compartment.

No cell sorting machine completely enclosed in a segregated environment has been made to date. Only parts of the entire cell sorter have been adapted to perform under controlled gas atmosphere such as the environmental containment system from DAKO but as mentioned above there is a need for a complete anoxic system to retain viability of anaerobic microorganisms. The generation of table top high speed sorters, such as the Becton Dickinson FACSAria, facilitates the process as its dimensions, configuration and features, such as computerized instrument control for the drop delay, fluidics stabilization, sample loading and fixed lasers that do not require alignment every day, makes the instrument amenable for high speed cell sorting by encasing it in a custom-made hood. It is understood that any other such instrument would function in the method.

The anaerobic samples or mixed cultures are introduced into the anaerobic cell sorter compartment (11) through the sample handling vestibule (12). In practice a container with the sample in a controlled environment is placed into the sample handling vestibule, which is then sealed by the closing of the external airlock. The vestibule is then flushed with one or more appropriate gases that remove atmospheric oxygen from the vestibule. Once the atmosphere of the vestibule and the sample handling compartments are compatible, the operator opens the airlock separating the vestibule and the cell sorter compartment. The operator can then open the sample container within the anoxic environment of the compartment to prepare the sample for introduction into the cell sorter without exposing the sample to oxygen. The sample, typically a liquid, is then placed in the injection port and run in the cell sorter. The cell sorter interrogates with a red, blue or violet laser the total of microdroplets with either developed colonies or labeled microdrops with a fluorescent dye or other molecule, as well as the number of microdrops lacking cells or cells not labeled. Additionally, the high speed cell sorter may analyze the pool of empty microbeads, the non-entrapped cells (cells that have outgrown the GMD or compartment) as well as the cells that formed a colony inside the microbead based only on light scatter properties. The detection of light scatter by microbeads or single cells is enhanced by a device such as the Forward Scatter Photomultiplier Tube developed by Becton Dickinson. This detection of bacterial or archaeal cells solely on light scatter was not possible in the past with standard light scatter diode detection. Also the pool of microdroplets may be detected based on the fluorescent properties such as those seen by differentially labeling detection reagents commonly used. The flow cytometer may count microdrops bearing first label only, microdrops bearing second label only, microdrops bearing both labels, and microdrops bearing neither label. In methods employing larger numbers of labels, still further categories of microdrops may be distinguished. The type of label present indicates the type and level of detection reagent present. Color compensation may be adjusted for spectral overlap using a color compensation kit.

Optionally, if anaerobes are naturally or artificially fluorescently labeled, flow cytometry analysis may be followed by sorting to make different populations of encapsulated anaerobes available for further analysis, such as microscopy and anaerobe cell culture line generation, DNA isolation, or culturing. High speed cell sorters separate individual anaerobes having defined properties, such as the presence of one or more particular secreted proteins, or degree of secretion level of one or more particular secreted proteins. Such anaerobes may then be further propagated for further analysis (e.g., to analyze DNA preparations from the anaerobes) or to generate one or more anaerobe lines. In some methods, gating strategies are used to focus the detection apparatus on a sub-population of microdrops containing a desired population of anaerobes. For example, forward or side scatter may be used to distinguish occupied from unoccupied microdrops. The occupied microdrops may then be further gated to detect a sub-population of anaerobes having a particular surface marker bound by a fluorescently labeled detection reagent. The gated subpopulation of anaerobes may then be analyzed for the presence of particular secreted proteins differentially labeled from the surface marker.

Additionally, anaerobic cells may be sorted directly into a subculture vessel such as a 96 well plate or a Hungate tube after detection with the cell sorting apparatus, such as the FACSAria, based on the forward and or side scatter and or some autofluorescent property of the cell(s), which could result from a naturally occurring pigment or fluorescent molecule or by addition of an artificial fluorescent dye.

Some methods use indirect sensing of detection reagent for signal amplification. For example, if the detection reagent is an antibody, it may be detected using a labelled antibody against the Ig isotype of interest. In other methods, an amplification cascade is employed. When this approach is used for detection, the primary detection reagent that binds to captured secreted molecules is a molecule, usually, an antibody labeled with horseradish peroxidase (HRP). The HRP is used to catalyze the deposition and binding of a labelled tyramide in microdrops that bind the HRP-labeled detection reagent. In turn, the label on the tyramide serves as binding sites for a secondary detection reagent that is typically labelled fluorescently, and has affinity for the label on the tyramide. Alternatively, light scatter properties may be used for the selection of the target population.

Subsequent to isolation and culturing of novel anaerobic microorganisms, individual organisms or populations of organisms may be used in a variety of industrial applications, such as for enhanced methane production in coal seams. Such applications have been described in detail including limitations and Benefits of Microbially Enhanced Coal bed Methane", A. R. Scott, Integras '95, May 15-19, 1995, The University of Alabama, Tuscaloosa, Ala.

In one embodiment, the step of sample collection may be followed by the steps of compartmentalization, incubation, and sorting (in any order), and the entire process may be performed anaerobically. In another embodiment, the step of sorting may be performed anaerobically, or the steps of incubation and sorting may be performed anaerobically, while the remaining steps may be performed aerobically. Further, the step of incubation may be optional and may be removed, for example, in the circumstance where it is no 1 required to separate and culture the cells.

While various embodiments and methods have been described herein, it should be understood that they have been presented by way of example only, and not limitation. Further, the breadth and scope of a preferred embodiment should not be limited by any of the above-described exemplary embodiments.

The following examples are offered to illustrate but not to limit the invention.

Example 1

Cultivation of Methanogens

Figure 5:
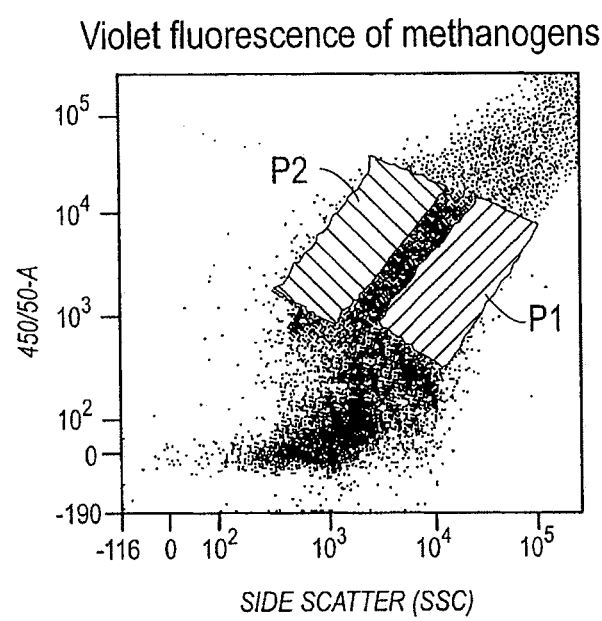
FIG. 5 show a scatter plot of a mixed population of methanogens and their violet autofluorescence.

An enrichment for the cultivation of methanogens was established using artificial media (Table 1) and a $H_2$:$CO_2$ as carbon and electron donor source. Cells from coalbed methane well water were inoculated into an artificial medium, and after 4 weeks of incubation a variety of cell morphologies appear in suspension. The samples were then plated onto agar media according to standard methods for culture purification. After 4 weeks colonies appear and were transfer again into liquid media with the goal of isolate pure cultures followed by another round of plating. The cultures appear to contain only two cell morphologies, putatively methanogenic Archaea corresponding to rods and cocci that could be seen as discrete populations in the FACSAria based on the forward and side scatter and violet autofluorescence from the F420 chromophores (See FIG. 4). Cells were then sorted aerobically in chilled media and immediately transferred to an anaerobic chamber for incubation and inspected for growth after 6 weeks without visible signs of cell growth (See FIG. 5).

Upon the set up of the anaerobic hood the same mixed culture with rods and cocci were sorted into sterile media under strict anaerobic conditions by depositing 1, 10, 100 and 1000 cells in separate tubes and sealed with butyl stoppers. After 5 weeks dense cell growth was observed in the 10 cells tube and a PCR amplification with Archaea and Bacteria primers revealed the single culture *Methanocalculus pumilus* and no signal with the Bacteria primer set.

TABLE 1

Medium composition for methanogenic enrichments and pure cultures

| Per 1 L of sterile produced water: | |
|---|---|
| $NH_4Cl$ | 0.5 g |
| $KH_2PO_4$ | 0.75 g |
| $K_2HPO_4$ | 1.5 g |
| commercial (ATCC) vitamin and trace element solution | 10 mL of each |
| After sterilization (1 atm, 15-30 min) from the stock solution: | |
| yeast extract | 0.05% final concentration |
| $Na_2S \times 9H_2O$ | 3 mM final concentration |
| cysteine-HCl | 3 mM final concentration |
| After sterilization (1 atm, 15-30 min) from the stock solution: Appropriate carbon&energy source for methanogenesis: | |
| gas mix | $CO_2:H_2/20:80$ up to 2 atm |

The invention claimed is:

1. An apparatus for sorting cells in a controlled environment, comprising:
 a sample handling vestibule linked to a cell sorting compartment via an airlock, wherein the cell sorting compartment comprises a cell sorter; and
 a fluidics compartment linked to the cell sorting compartment by one or more fluidics tubes and a chamber equalization tube,
 wherein the cell sorter and the fluidics compartment are completely enclosed in the controlled environment.

2. The apparatus of claim 1, wherein the controlled environment is an anoxic environment.

3. The apparatus of claim 1, further comprising a temperature regulating device.

4. The apparatus of claim 1, further comprising an oxygen sensor.

5. The apparatus of claim 1 wherein the cell sorting compartment further comprises one or more chamber gloves.

6. The apparatus of claim 1 wherein the sample handling vestibule is connected to a gas source allowing for creation of an anoxic atmosphere within the sample handling vestibule.

7. The apparatus of claim 1 wherein the fluidics compartment comprises a fluidics pump.

8. The apparatus of claim 1 wherein the cell sorter is driven by an anaerobic gas.

9. The apparatus of claim 1 wherein the fluidics compartment is segregated from the cell sorter.

10. The apparatus of claim 1 wherein the controlled environment is an anoxic environment.

\* \* \* \* \*